(12) United States Patent
Klusener et al.

(10) Patent No.: US 9,567,273 B2
(45) Date of Patent: Feb. 14, 2017

(54) PROCESS FOR PREPARING ALKYLATE COMPRISING AN IMPROVED SOLIDS REMOVAL STEP

(71) Applicants: SHELL OIL COMPANY, Houston, TX (US); CHINA UNIVERSITY OF PETROLEUM, Beijing (CN)

(72) Inventors: Peter Anton August Klusener, Amsterdam (NL); Zhichang Liu, Beijing (CN); Xianghai Meng, Beijing (CN); Rui Zhang, Beijing (CN); Jan De With, Amsterdam (NL); Chunming Xu, Beijing (CN)

(73) Assignee: SHELL OIL COMPANY, Houston, TX (US)

( * ) Notice: Subject to any disclaimer, the term of this patent is extended or adjusted under 35 U.S.C. 154(b) by 30 days.

(21) Appl. No.: 14/651,405

(22) PCT Filed: Dec. 13, 2013

(86) PCT No.: PCT/EP2013/076607
§ 371 (c)(1),
(2) Date: Jun. 11, 2015

(87) PCT Pub. No.: WO2014/091013
PCT Pub. Date: Jun. 19, 2014

(65) Prior Publication Data
US 2015/0315103 A1    Nov. 5, 2015

(30) Foreign Application Priority Data
Dec. 13, 2012   (WO) ................ PCT/CN2012/086527

(51) Int. Cl.
*C07C 2/56*       (2006.01)
*C07C 2/58*       (2006.01)
(Continued)

(52) U.S. Cl.
CPC .............. *C07C 7/005* (2013.01); *C07C 2/58* (2013.01); *C10G 29/205* (2013.01); *C10G 31/09* (2013.01);
(Continued)

(58) Field of Classification Search
CPC ............... C07C 2/56; C07C 2/58; C07C 2/60; C07C 2/62
(Continued)

(56) References Cited

U.S. PATENT DOCUMENTS 7,285,698 B2    10/2007   Liu et al.
2012/0178982 A1*  7/2012  Liu .......................... C07C 2/60
                                                    585/716

FOREIGN PATENT DOCUMENTS

WO    2011015639    2/2011
WO    2011015661    2/2011

OTHER PUBLICATIONS

Albright, L.F.; "Present & Future Alkylation Processes in Refineries", American Chemical Society, Ind. Eng. Res, vol. 48, No. 3, pp. 1409-1413; 2009.
(Continued)

*Primary Examiner* — Thuan D Dang

(57) ABSTRACT

The present invention relates to a process for preparing alkylate comprising the subsequent steps (a), (b) and (c):
(a) an alkylation step, wherein in a reaction zone a hydrocarbon mixture comprising at least an isoparaffin and an olefin is reacted with an ionic liquid catalyst to obtain an effluent comprising alkylate and solids, which latter are formed as side products in the alkylation step;
(b) a separation step, wherein at least part of the alkylate-comprising effluent coming from the reaction zone is separated in a separator unit into a hydrocarbon-rich phase and an ionic liquid catalyst-rich phase which latter
(Continued)

phase also comprises solids formed as side products during the alkylation reaction; and (c) a solids removal step, wherein the solids in ionic liquid catalyst-rich phase are separated from the ionic liquid catalyst using a suitable separating device;

wherein the process further comprises a step following the separation step (b) and prior to the solids removal step (c).

10 Claims, 5 Drawing Sheets

(51) Int. Cl.
  *C07C 2/60* (2006.01)
  *C07C 2/62* (2006.01)
  *C07C 7/00* (2006.01)
  *C10G 29/20* (2006.01)
  *C10G 31/09* (2006.01)
  *C10G 31/10* (2006.01)

(52) U.S. Cl.
  CPC .......... *C10G 31/10* (2013.01); *C07C 2521/02* (2013.01); *C07C 2523/72* (2013.01); *C07C 2527/10* (2013.01); *C07C 2527/126* (2013.01); *C07C 2531/02* (2013.01); *C10G 2300/1088* (2013.01); *C10G 2400/02* (2013.01); *Y02P 20/542* (2015.11)

(58) Field of Classification Search
  USPC ................................. 585/719, 722, 727, 902
  See application file for complete search history.

(56) References Cited

OTHER PUBLICATIONS

Corma, Avelino, et al.; "Chemistry, Catalysts, and Processes for Isoparaffin-Olefin Alkylations Actual Situation & Future Trends"; Catalysis Reviews: Science & Engineering, vol. 35; No. 4, pp. 483-570, 1993.

Liu, et al.; "Ionic Liquid Alkylation Process Produces High-Quality Gasoline"; Oil & Gas Journal.; vol. 104, No. 40; pp. 52-56; 2006.

* cited by examiner

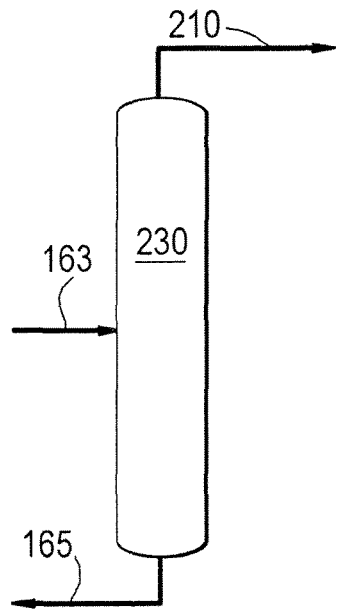
Fig.1.1
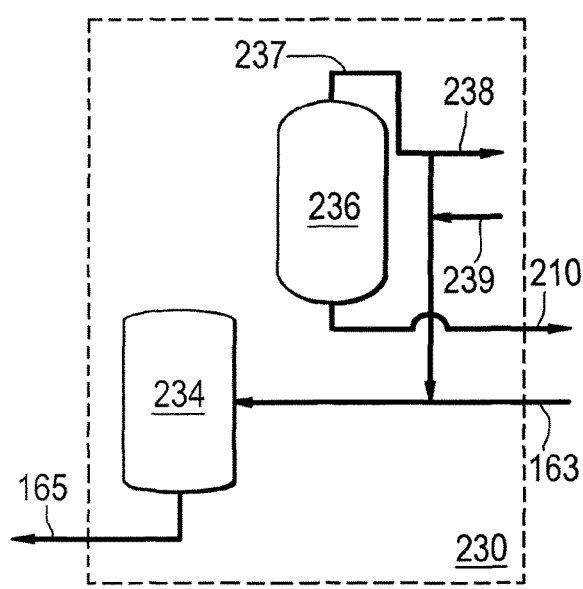
Fig.1.2
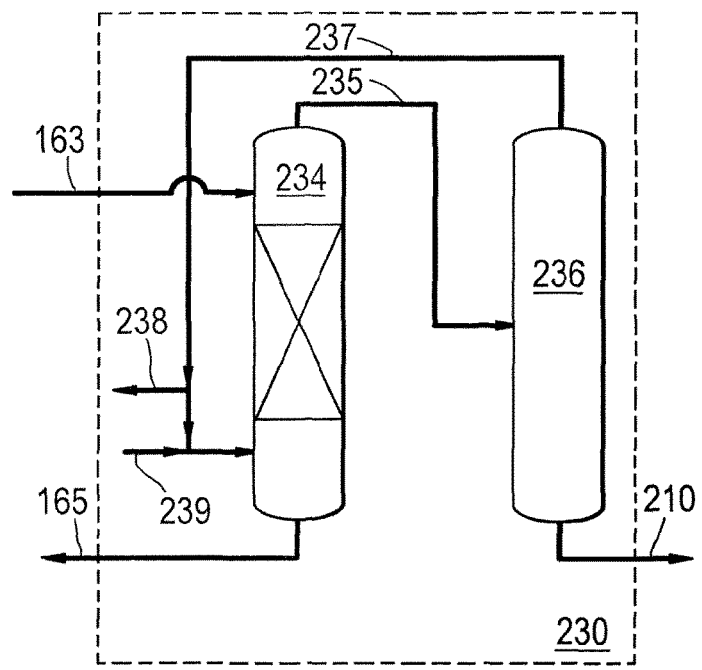
Fig.1.3

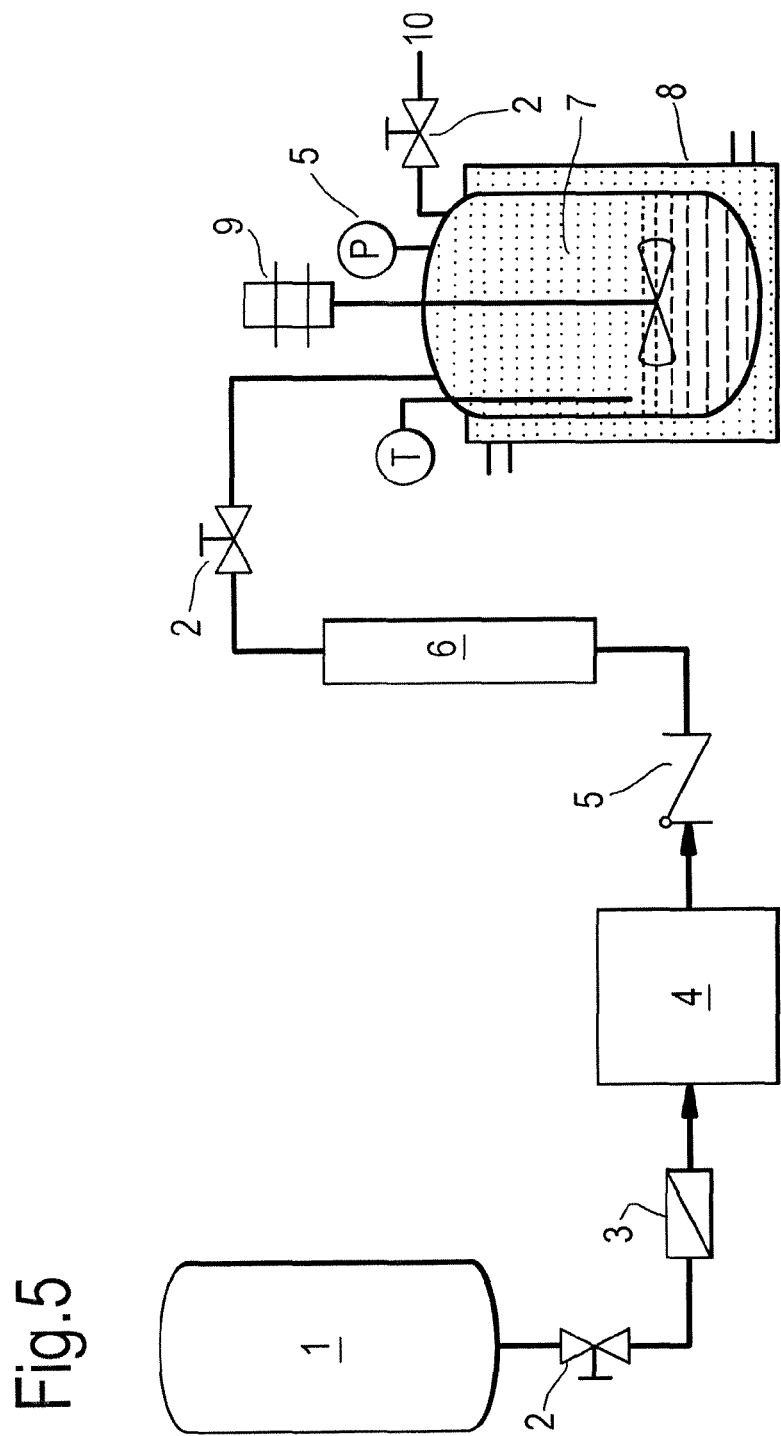

PROCESS FOR PREPARING ALKYLATE COMPRISING AN IMPROVED SOLIDS REMOVAL STEP

PRIORITY CLAIM

The present application is the National Stage (§371) of International Application No. PCT/EP2013/076607, filed Dec. 13, 2013, which claims priority from PCT/CN2012/086527, filed Dec. 13, 2012 incorporated herein by reference.

FIELD OF THE INVENTION

The present invention provides a process for the preparation of alkylate using an ionic liquid catalyst comprising an improved solids removal step.

BACKGROUND OF THE INVENTION

There is an increasing demand for alkylate fuel blending feedstock. As a fuel-blending component alkylate combines a low vapour pressure, no sulfur, olefins or aromatics with high octane properties. The most desirable components in the alkylate are trimethylpentanes (TMPs), which have research octane numbers (RONs) of greater than 100. Such an alkylate component may be produced by reacting isobutane with a butene or a mixture of butenes in the presence of a suitable acidic catalyst, e.g. HF or sulfuric acid, although other catalysts such a solid acid catalyst have been reported. Recently, the alkylation of isoparaffins with olefins using an acidic ionic liquid catalyst has been proposed as an alternative to HF and sulfuric acid catalysed alkylation processes.

For instance, U.S. Pat. No. 7,285,698 discloses a process for manufacturing an alkylate oil, which uses a composite ionic liquid catalyst to react isobutane with a butene. In the process of U.S. Pat. No. 7,285,698, isobutane and a butene are supplied to a reactor and the alkylate is formed by contacting the reactants with a composite ionic liquid under alkylation conditions. The reactor effluent is separated and the ionic liquid phase is recycled to the reactor while the hydrocarbon phase is treated to retrieve the alkylate. However, during operation of such an ionic liquid alkylation process solids are formed. As the reaction progresses, these solids accumulate in the reaction zone and may lead to blockage of pathways and/or valves. In WO2011/015639 a process is described for removal of the solids formed during the ionic liquid alkylation process. According to that process, a solids-comprising effluent comprising hydrocarbons and acidic ionic liquid is withdrawn from the reaction zone and at least part of the solids-comprising effluent is treated to remove at least part of the solids to obtain a solids-depleted effluent. It has however been found that solids removal according to the process of WO2011/015639 is difficult because of high viscosity of the ionic liquid. Centrifugation of the solids-comprising effluent is therefore complex and is accompanied by high energy consumption. Filtration is not very practical because it is time consuming and requires high pressures. Finally, settling is even more time consuming and therefore not a desirable solution.

SUMMARY OF THE INVENTION

It has now been found that the solids formed in an ionic liquid alkylation process can be removed from the ionic liquid much easier and much more efficiently by adding an amount of an organic solvent prior to the solids removal step.

Accordingly, the present invention provides a process for preparing alkylate comprising the subsequent steps (a), (b) and (c):

(a) an alkylation step, wherein in a reaction zone a hydrocarbon mixture comprising at least an isoparaffin and an olefin is reacted with an ionic liquid catalyst to obtain an effluent comprising alkylate and solids, which latter are formed as side products in the alkylation step;

(b) a separation step, wherein at least part of the alkylate-comprising effluent coming from the reaction zone is separated in a separator unit into a hydrocarbon-rich phase and an ionic liquid catalyst-rich phase which latter phase also comprises solids formed as side products during the alkylation reaction; and (c) a solids removal step, wherein the solids in ionic liquid catalyst-rich phase are separated from the ionic liquid catalyst using a suitable separating device;

wherein the process further comprises a step following the separation step (b) and prior to the solids removal step (c), wherein an amount of an organic solvent is added to the ionic liquid catalyst-rich phase, which organic solvent has a viscosity which is significantly lower than that of the ionic liquid and which solvent is at least partially miscible with the ionic liquid. The solvent may be removed after the solids removal step.

An advantage of the present invention is that ionic liquid can be extracted from the solid with an organic solvent and easily recovered by evaporation of the solvent.

Another advantage is that that ionic liquid extracted from the solid can be reused in the ionic liquid alkylation ionic liquid alkylation process without significant loss of selectivity.

BRIEF DESCRIPTION OF THE DRAWINGS

In FIGS. 1.1, 1.2 and 1.3 the effect is shown of the mass fraction of an organic solvent (toluene and DCM, respectively) on viscosities of composite ionic liquid (CIL)+ organic solvent mixtures at 20° C. and 30° C.

FIG. 5 is a schematic representation of a continuous extraction apparatus as used in examples 8 and 9.

DETAILED DESCRIPTION OF THE INVENTION

Figure 1:
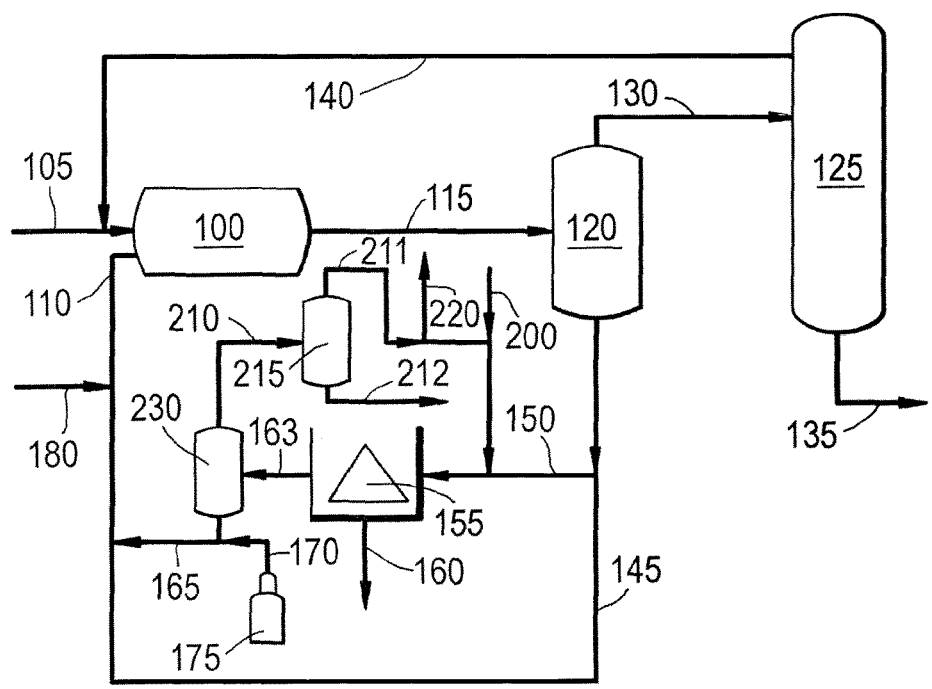
In FIG. 1, a schematic representation is given of a process according to the invention.

The ionic liquid alkylation process of the invention is a process wherein an alkylate is prepared by reacting an isoparaffin with an olefin, in particular isobutane and a butene or a mixture of butenes. The obtained alkylate is particularly suitable for gasoline blending purposes or for use in aviation gasoline production. In the alkylation process, the isoparaffin and the olefin are provided to a reaction zone. In the reaction zone a hydrocarbon mixture comprising isoparaffin and olefin is contacted with a catalyst suitable for alkylation. The hydrocarbon mixture comprises olefin, which is typically supplied externally, i.e. fresh olefin, and comprises isoparaffin. The isoparaffin may be externally supplied isoparaffin, i.e. fresh isoparaffin, and/or isoparaffin which is recycled from any other part of the process. The (fresh) isoparaffin and olefin may be supplied to the process separately, however typically the (fresh) isoparaffin and the (fresh) olefin are provided to the reaction zone as a mixture comprising isoparaffin and olefin.

According to the present process the alkylation catalyst is a composite ionic liquid mixture. Ionic liquids are known in the art for their ability to catalyse alkylation reactions. The catalyst used in the present alkylation process is a composite ionic liquid comprising cations derived from a hydrohalide of an alkyl-containing amine, imidazolium or pyridine. Preferably, the cations comprise cations of ammonium salts, for example nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of preferred ammonium cations include triethylammonium ($NEt_3H^+$) and methyldiethyl-ammonium cations ($MeNEt_2H^+$), cations in which the nitrogen is part of a cyclic structure (e.g. like in piperidine and pyrrolidine) or

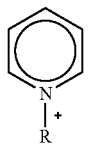

The anions of the composite ionic liquid are preferably derived from aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulfate or nitrate to form a coordinate anion, in particular a coordinate anion derived from two or more metal halides, wherein at least one metal halide is an aluminium halide. Suitable further metal halides, sulfates or nitrates, may be selected from halides, sulfates or nitrates of metals selected from the group consisting of Group IB elements of the Periodic Table, Group IIB elements of the Periodic Table and transition elements of the Periodic Table. Preferred metals include copper, iron, zinc, nickel, cobalt, molybdenum, silver or platinum. Preferably, the metal halides, sulfates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

As mentioned herein above, the hydrocarbon mixture comprising isoparaffin and olefin is contacted with the catalyst in the reaction zone. The hydrocarbon mixture is mixed in the reaction zone with the catalyst to form a reaction mixture. Mixing may be done by any suitable means for mixing two or more liquids, including dynamic and static mixers. In contact with the catalyst, the isoparaffins and olefins react under alkylation conditions to form alkylate. As the reaction progresses, the mixture in the reaction zone will, besides hydrocarbon reactants and acidic ionic liquid, additionally comprise products.

The formed alkylate is obtained from the reaction zone in the form of an alkylate-comprising effluent. The alkylate-comprising effluent still comprises a substantial amount of unreacted isoparaffin. Therefore, part of the alkylate-comprising effluent may be recycled to the reaction zone to maintain a high ratio of isoparaffin to olefin in hydrocarbon mixture in the reaction zone.

At least part of the alkylate-comprising effluent of the reaction zone is separated in a separator unit into a hydrocarbon-rich phase and an ionic liquid catalyst-rich phase. At least part of the hydrocarbon-rich phase is treated and/or fractionated (e.g. by distillation) to retrieve the alkylate and optionally other components in the hydrocarbon phase, such as unreacted isoparaffin or n-paraffins. Preferably, such isoparaffin is at least partly reused to form part of the isoparaffin feed provided to the process. This may be done by recycling at least part of the isoparaffin, or a stream comprising isoparaffin obtained from the fractionation of the hydrocarbon-rich phase, and combining it with the isoparaffin feed to the process.

Reference herein to a hydrocarbon-rich phase is to a phase comprising more than 50 mol % of hydrocarbons, based on the total moles of hydrocarbon and ionic liquid catalyst.

Reference herein to an ionic liquid catalyst-rich phase is to a phase comprising more than 50 mol % of ionic liquid catalyst, based on the total moles of hydrocarbon and ionic liquid catalyst.

Due to the low affinity of the ionic liquid for hydrocarbons and the difference in density between the hydrocarbons and the ionic liquid catalyst, the separation between the two phases is suitably done using for example well known settler means, wherein the hydrocarbons and catalyst separate into an upper predominantly hydrocarbon phase and lower predominantly catalyst phase or by using any other suitable liquid/liquid separator. Such liquid/liquid separators are known to the skilled person and include cyclone and centrifugal separators. The catalyst phase is generally recycled back to the reactor.

As described herein before, during the alkylation reaction solids are formed. Reference herein to solids is to non-dissolved solid particles. The solids predominantly consist of metals, metal compounds and/or metal salts which were originally comprised in the composite ionic liquid catalyst. Typically, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise contaminant components, which were introduced into the reaction mixture as contaminants in the hydrocarbon mixture or the composite ionic liquid. Alternatively, (part of) the solids may be the product of a chemical reaction involving any of the above-mentioned compounds, e.g. polymeric substances.

The solids may have any size, however the solids typically have an average size of in the range of from 0.1 to 10 μm. In particular, at least 50% of the solids have a particle size below 5 μm, more particular 80% of the solids have a particle size below 5 μm based on the total number of solid particles.

In WO2011/015639 it is described that although during mixing these solids are dispersed throughout the reaction mixture, upon separation of the alkylate-comprising effluent it was found that the solids to a large extent accumulate in the composite ionic liquid catalyst-rich phase. If the catalyst-rich phase would subsequently be recycled to the reaction zone to become part of the reaction mixture in the reaction zone, the solids would accumulate in the reaction zone, resulting in undesirably high solids content in the reaction zone. A high solids content in the reaction zone may for instance result in blockage of pathways or valves in the reactor zone and pipes to and from the separation unit, due to precipitation of solids. In addition, at high solids content the solids may agglomerate to form large aggregates, resulting in increased blockage risk. Therefore, at least part of the solids needs to be removed from the ionic liquid catalyst-rich phase. It is not required to remove all solids. Preferably, solids are removed to an extent that the reaction mixture (i.e. a mixture comprising hydrocarbon reactants, composite ionic liquid and products) comprises in the range of from 0.05 to 5 wt %, more preferably at most 2 wt % of solids, based on the total weight composite ionic liquid in the reaction zone.

According to the present invention, the organic solvent that is added to the ionic liquid catalyst-rich phase may be any suitable organic solvent having a viscosity which is significantly lower than that of the ionic liquid and being at least partially miscible with the ionic liquid. Preferably, the organic solvent is selected from the group of aromatic solvents (such as benzene and toluene), halogenated aliphatic hydrocarbons (such as dichloromethane), acetonitrile, and the like, or mixtures thereof. Preferably the organic solvent is selected from benzene, toluene, dichloromethane and acetonitrile, more preferably from toluene and dichloromethane and most preferably the organic solvent is toluene.

In a further embodiment of the invention, the mass fraction of the organic solvent, when added to the ionic liquid catalyst-rich phase, is 5-60 wt %, preferably at least 10 wt %, more preferably 10-50 wt %, alternatively at least 15 wt %, and most preferably 20-50 wt %.

According to the invention, the solids are removed from the reaction zone in a solids-comprising effluent which is introduced into a separator unit. In this separator unit the effluent is separated into an ionic liquid catalyst-rich phase and a hydrocarbon-rich phase. The ionic liquid catalyst-rich phase is transferred through a pipeline connection to a solid separating device. In a further embodiment of the invention, the organic solvent is added via a pipeline by in-line mixing in the pipeline connection between the separator unit and the solid separating device. However, it is also an embodiment of the invention to add the organic solvent to ionic liquid catalyst-rich phase in a mixing vessel located in between the pipeline connection between the separator unit and the solid separating device.

Subsequently, at least part of the solids in the mixture of the ionic liquid catalyst-rich phase and the organic solvent is removed. After the removal of solids a solids-depleted effluent is obtained.

The solids may be removed by any suitable means for removing solids from liquids, including but not limited to filtration, precipitation (e.g. in a settler unit) and centrifugation processes, and processes using a cyclone. Such processes are well known in the art. In view of process efficiency, centrifugation is the preferred process for removing the solids from the ionic liquid catalyst-rich phase. Due to the specific nature of ionic liquids it is preferred that the removal of the solids is performed at such a temperature that the ionic liquid catalyst is liquid. In particular, it is preferred to remove the solids at a temperature in the range of from 5 to 80° C., more preferably of from 20 to 60° C. At elevated temperatures, the viscosity of the ionic liquid or ionic liquid/solvent mixture is lower while the density is reduced, which may be beneficial in view of decreased time and power input required to obtained separation of the solids from the liquid.

The solids may be removed from the process in any form, however typically the solids are removed in the form of a paste of solids. Such a paste may comprise next to solid particles for instance some residual ionic liquid, residual solvent and/or hydrocarbons (which may be for instance some polymeric material formed as side product during the reaction). Depending on the amount of residual liquid phase, the solids may also be removed from the process in the form of a slurry. In this text, the term "paste" is meant to also refer to "slurry". Typically, a paste contains at least 30% of solid particles.

In an embodiment of the invention, the solids removed from the process are regenerated to be re-used in the alkylation process. In such regeneration process the solids are preferably treated in the form of a paste. A preferred process is a process wherein a first ionic liquid is used as a catalyst which is a composite ionic liquid comprising ammonium cations, and anions being composite coordinate anions derived from two or more metal salts, wherein at least one metal salt is an aluminium salt and any further metal salt is a salt of a metal selected from the group consisting of Group IB elements of the Periodic Table, Group IIB elements of the Periodic Table and transition elements of the Periodic Table, the regeneration process comprising removing the solids from the reaction zone of the alkylation process and subsequently treating the solids with a second ionic liquid made from an ammonium salt as cation, and an aluminium salt as anion which is the same as the aluminium salt present in the first ionic liquid.

According to the invention, a solids-depleted effluent results after solids removal, which effluent comprises ionic liquid catalyst and the organic solvent that was added to improve solids removal. In a further embodiment the process of the invention comprises removal of the organic solvent after solids removal. The organic solvent is removed from the effluent by appropriate means. Preferably, the solvent is removed by evaporation (if the boiling point of the solvent is low) or by extraction, for example by alkane extraction, preferably using isobutane or the alkylate product, and most preferably, isobutane is used for the extraction, after which the solvent is separated from the alkane by means of distillation. Suitably, the organic solvent is removed by a distillation unit or isobutane extraction followed by distillation, more preferably by isobutane countercurrent extraction followed by distillation.

Preferably, the organic solvent is purified by distillation device, from which the heavy ends (high boiling point components) is removed.

In an embodiment of the invention, the organic solvent is recycled to separator unit.

In an embodiment of the invention solvent removal takes place in a solvent removal unit, located after the outlet of the solid separating device. The solvent may be recycled for further use in the solids separation step. In a further embodiment of the invention, the resulting ionic liquid is recycled to the reaction zone and re-used in the alkylation process.

Some further process details of the alkylation process are described below.

In the alkylation process, an isoparaffin and an olefin are reacted to form alkylate by contacting a hydrocarbon mixture comprising isoparaffin and olefin with a catalyst under alkylation conditions. Preferably, the hydrocarbon mixture comprises at least isobutane and optionally isopentane, or a mixture thereof, as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of a continuous process, excess isoparaffin can be recycled for reuse in the hydrocarbon mixture.

The alkylation conditions (or process conditions) are those known in the art for this type of alkylation processes. Actual operational process conditions are for example dependent of the exact composition of the hydrocarbon mixture and catalyst, and the like.

The temperature in the alkylation reactor is preferably in the range of from −20 to 100° C., more preferably in the range of from 0 to 50° C. In any case the temperature must be high enough to ensure that the ionic liquid catalyst is in the liquid state.

To suppress vapour formation in the reactor, the process may be performed under pressure; preferably the pressure in the reactor is in the range of from 0.1 to 1.6 MPa.

Preferably, the composite ionic liquid catalyst-rich phase to hydrocarbon-rich phase volume ratio in the alkylation reaction zone is at least 0.5, preferably 0.9 more preferably at least 1. Preferably, the composite ionic liquid catalyst-rich phase to hydrocarbon-rich phase volume ratio in the reaction zone is in the range of from 1 to 10.

The hydrocarbon mixture may be contacted with the catalyst in any suitable alkylation reactor. The hydrocarbon mixture may be contacted with the catalyst in a batch-wise, a semi-continuous or continuous process. Reactors such as used in liquid acid catalysed alkylation can be used (see L. F. Albright, Ind. Eng. Res. 48 (2009)1409 and A. Corma and A. Martinez, Catal. Rev. 35 (1993) 483); alternatively the reactor is a loop reactor, optionally with multiple injection points for the hydrocarbon feed, optionally equipped with static mixers to ensure good contact between the hydrocarbon mixture and catalyst, optionally with cooling in between the injection points, optionally by applying cooling via partial vaporization of volatile hydrocarbon components (see Catal. Rev. 35 (1993) 483), optionally with an outlet outside the reaction zone (see WO2011/015639). In the prior art diagrams are available of alkylation process line-ups which are suitable for application in the process of this invention, e.g. in U.S. Pat. No. 7,285,698, Oil & Gas J., vol 104 (40) (2006) p 52-56 and Catal. Rev. 35 (1993) 483.

LEGENDS AND DETAILED DESCRIPTION OF THE FIGURES

In FIG. 1 a schematic representation is given of a process according to the invention.

In FIG. 1a a schematic representation of a solvent distillation unit.

In FIG. 1b a schematic representation is given of a solvent extraction unit.

In FIG. 1c a schematic representation is given of a solvent counter-current extraction unit.

Figure 2:
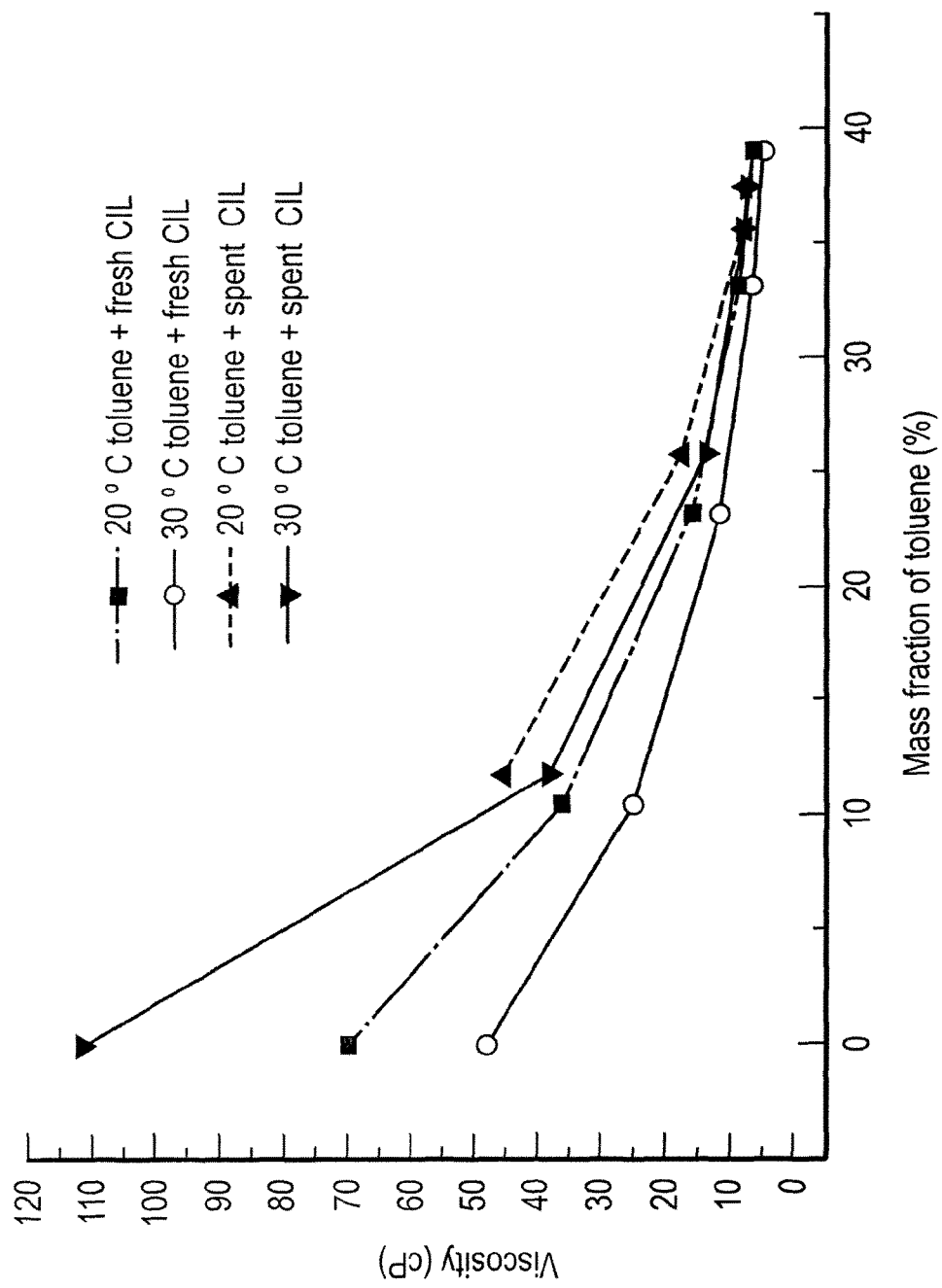
In FIG. 2 the viscosities of ionic liquid-toluene mixtures as a function of toluene contents are shown.

In FIG. 2 the viscosities of ionic liquid-toluene mixtures as a function of toluene contents are shown.

Figure 3:
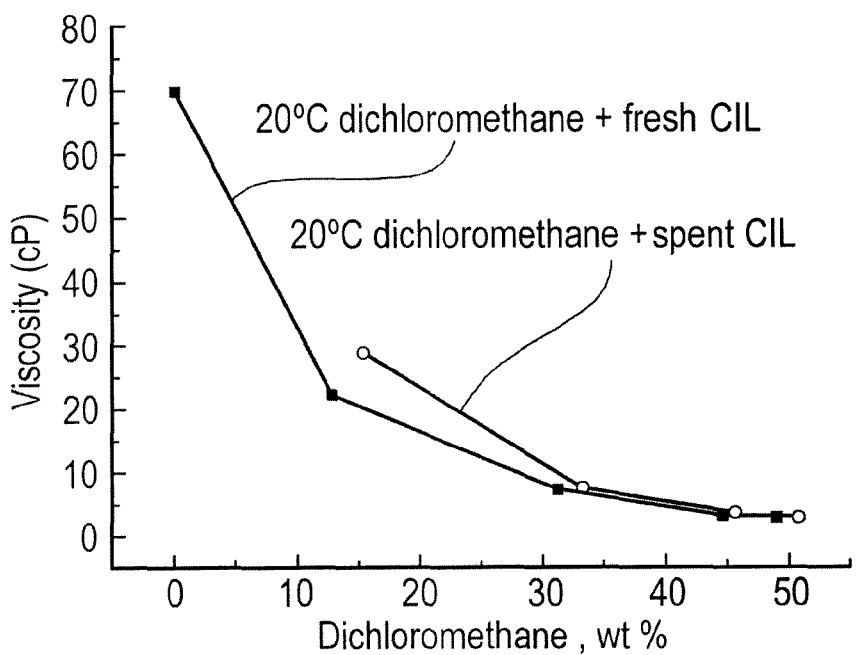
In FIGS. 3 and 4 the viscosities of the ionic liquid-dichloromethane mixtures as a function of dichloromethane contents are shown at 20 and 30 OC, respectively.
Figure 4:
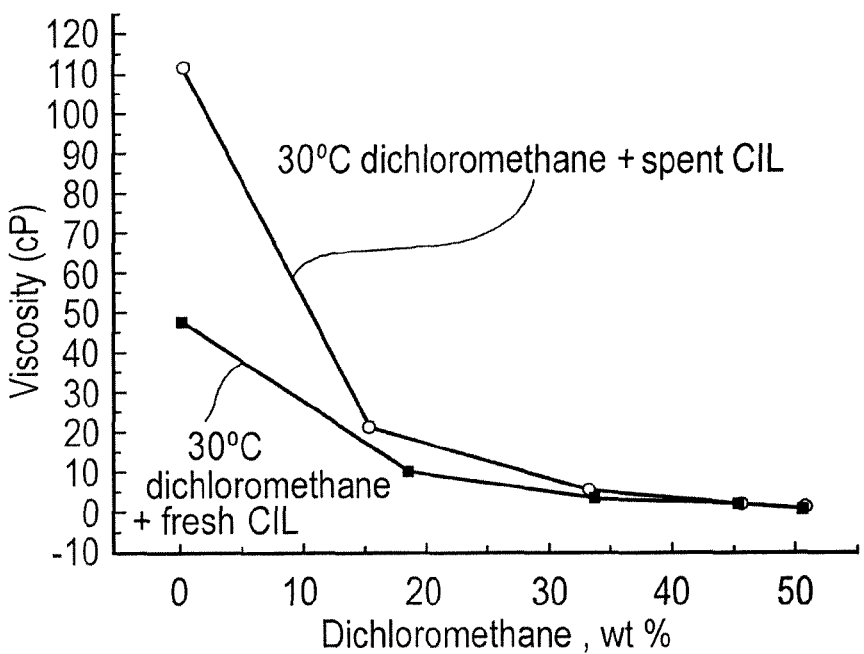

In FIGS. 3 and 4 the viscosities of the ionic liquid-dichloromethane mixtures as a function of dichloromethane contents are shown at 20 and 30° C., respectively.

FIG. 5 is a schematic representation of a continuous extraction apparatus as used in examples 8 and 9.

In FIG. 1, a mixture, comprising olefin and isoparaffin is provided to reactor 100 through line 105. Composite ionic liquid catalyst is also provided to reaction zone 100 through line 110. In reaction zone 100, the hydrocarbon mixture and catalyst are mixed under alkylation conditions. Through line 115, a solids-comprising effluent comprising hydrocarbons and ionic liquid is withdrawn from the reaction zone. Part of this effluent may be directly recycled to the reactor or combined with line 105 via a recycle line (not shown). At least part of the effluent is supplied to liquid/liquid separation unit 120, e.g. a settler unit. In liquid/liquid separation unit 120, a hydrocarbon-rich phase and ionic liquid catalyst-rich phase separate under influence of gravity or centrifugal forces. Part of the hydrocarbon-rich phase may be directly recycled to the reactor or combined with line 105 via a recycle line (not shown). At least part of the hydrocarbon-rich phase is provided to fractionator 125 through line 130. From the bottom of fractionator 125, an alkylate-comprising product is retrieved through line 135. The alkylate-comprising product can be used for instance for fuel blending purposes. Additionally, an isoparaffin-comprising stream is retrieved from fractionator 125, which is recycled via line 140 to become part of the mixture in line 105. Other hydrocarbon-comprising streams (not shown) may also be retrieved from fractionator 125.

The ionic liquid catalyst-rich phase can be recycled via line 145 to reactor 100. Part or all of the catalyst can be diverted from line 145 by line 150 to solids separating device 155 (e.g. a centrifuge). Organic solvent is added via a pipe either in line 150. In device 155, solids are removed from the ionic liquid catalyst phase and are retrieved via line 160, after which the solids may be regenerated and recycled to the reaction zone. The remaining ionic liquid catalyst effluent mixture exits device 155 via line 163. The organic solvent is removed after the effluent mixture exits device 155, preferably directly after exiting, in solvent separation unit 230 (e.g. a flash vessel). Preferably, the solvent is removed by isobutane extraction followed by distillation. A schematic representation of a solvent distillation unit is shown in FIG. 1a. A schematic representation of a solvent extraction unit is shown in FIG. 1b. In this extraction unit the effluent 163 is mixed with the extraction solvent from distillation device 236 via line 237 and sent to settling device 234. In settling device the ionic liquid catalyst is removed via line 165 and the extract liquid is sent via line 235 to distillation device 236, from which the solvent is removed via line 210 and the extract solvent is removed via line 237. Extract solvent can optionally removed via bleed line 238 and added to the system via make up line 239. Preferably, the solvent is removed by isobutane counter-current extraction tower followed by distillation. A schematic representation of a solvent counter-current extraction unit is shown in FIG. 1c. In this extraction unit the effluent 163 is sent via line 235 to the top of counter-current extraction tower 234. And the extract solvent (isobutane) sent to the bottom of counter-current extraction tower 234. After counter-current extraction, the ionic liquid catalyst is removed via line 165 and the extract liquid is sent via line 235 to distillation device 236, from which the solvent is removed via line 231 and the extract solvent is removed via line 237. Extract solvent can optionally be removed via bleed line 238 and added to the system via make up line 239. Preferably, the solvent is purified by distillation device 215, from which the heavy ends (high boiling point components) is removed via line 212, and the solvent is recycled via line 211, which line is provided with line 220 for solvent bleed—when necessary—and line 200 for external solvent addition.

Optionally, for rejuvenation of the ionic liquid catalyst hydrochloride gas may be provided to the ionic liquid catalyst via line 170 from gas container 175. Optionally, a mixing device (not shown), e.g. a venturi absorber, is used to mix the hydrogen chloride gas into line 165. By allowing part of the catalyst to bypass the hydrogen chloride rejuvenation via line 145, any remaining gaseous hydrogen chloride may react with the ionic liquid catalyst in line 145 when lines 165 and 145 come together.

The resulting ionic liquid catalyst is subsequently directed back to reaction zone 100. If necessary, additional fresh ionic liquid catalyst or externally supplied spent ionic liquid catalyst can be provided to the reaction zone 100 via line 180.

The invention is illustrated by the following non-limiting examples.

EXAMPLE 1

Viscosity Measurements

1.1 Viscosity of Toluene and Ionic Liquids

Under atmospheric pressure, at 20° C. and at 30° C., respectively, the viscosities of mixtures of fresh composite ionic liquid (CIL, prepared according to U.S. Pat. No. 7,285,698) and toluene, and of mixtures of spent (used) CIL and toluene were measured. The spent CIL was taken from the catalyst-comprising effluent from an ionic liquid alkylation process as described in WO2011/015639. The results are summarized in Table 1.1.

TABLE 1.1

Viscosities (in cP) of toluene-fresh CIL and toluene-spent CIL mixtures at 20° C. and at 30° C.

| Toluene-fresh CIL | | | | | |
|---|---|---|---|---|---|
| Mass fraction of toluene, % | 0 | 10.47 | 23.14 | 33.11 | 39.01 |
| 20° C. | — | 36.13 | 15.74 | 8.43 | 6.15 |
| 30° C. | 47.83 | 24.93 | 11.49 | 6.43 | 4.76 |
| Toluene-spent CIL | | | | | |
| Mass fraction of toluene, % | 0 | 11.76 | 25.74 | 35.61 | 37.45 |
| 20° C. | — | 45.3 | 17.43 | 7.72 | 7.44 |
| 30° C. | 111.54 | 38.17 | 13.63 | 7.85 | 7.16 |

The viscosities of the mixtures as a function of toluene contents are shown in FIG. 2.

The measurements show that at both temperatures the viscosity of toluene-used CIL is higher than that for toluene-fresh CIL at the same mass fraction of toluene, and is nearly the same when the mass fraction of toluene is higher than 35%. When the mass fraction of toluene is less than 15%, viscosities at the measured temperatures for both fresh CIL and spent CIL show a steep decrease with increase of the mass fraction of toluene. When the mass fraction of toluene is between 15% and 35%, viscosities for both fresh CIL and spent CIL show lighter decrease. When the mass fraction of toluene is between 35% and 40%, viscosities for both fresh CIL and spent CIL show almost no change any more. The viscosity of toluene is significantly lower than that of CIL. Therefore at higher toluene contents, the viscosities for CIL+toluene mixtures will finally decrease to the toluene viscosity (0.44 cP at 30° C.).

1.2 Viscosity of Dichloromethane and Ionic Liquids

Under atmospheric pressure, at 20° C. and at 30° C., respectively, the viscosities of mixtures of fresh composite ionic liquid (CIL, prepared according to U.S. Pat. No. 7,285,698) and dichloromethane (DCM), and of mixtures of spent (used) CIL and DCM were measured. The spent CIL was taken from the catalyst-comprising effluent from an ionic liquid alkylation process as described in WO2011/015639. Solids have been removed.

The results are summarized in Table 1.2.

TABLE 1.2

Viscosities (in cP) of DCM-fresh CIL and DCM-spent CIL mixtures at 20° C. and at 30° C.

| DCM-fresh CIL | | | | | |
|---|---|---|---|---|---|
| Mass fraction of DCM, % | 0 | 12.79 | 31.21 | 44.58 | 48.93 |
| 20° C. | 69.79 | 22.31 | 7.38 | 3.36 | 2.94 |
| 30° C. | 47.83 | 10.69 | 4.57 | 3.34 | 2.17 |
| DCM-spent CIL | | | | | |
| Mass fraction of DCM, % | 0 | 15.36 | 33.25 | 45.58 | 50.73 |
| 20° C. | — | 29.01 | 7.64 | 3.76 | 2.97 |
| 30° C. | 111.54 | 21.67 | 6.40 | 3.17 | 2.53 |

The viscosities of the mixtures as a function of DCM contents are shown in FIG. 3 and FIG. 4.

The measurements show that at both temperatures the viscosity of the DCM-spent CIL mixture is higher than that of the DCM-fresh CIL mixture at the same mass fraction of DCM, and nearly the same when the mass fraction of DCM is higher than 35%. When the mass fraction of DCM is less than 15%, viscosities at the measured temperatures for both fresh CIL and spent CIL show a steep decrease with increase of the mass fraction of DCM. When the mass fraction of DCM is between 15% and 35%, viscosities of both fresh CIL and spent CIL show lighter decrease. When the mass fraction of DCM is between 35% and 50%, viscosities for both fresh CIL and spent CIL show almost no change any more. The viscosity of DCM is significantly lower than that of CIL. Therefore at higher DCM contents, the viscosities for CIL+DCM mixtures will finally decrease to the DCM viscosity (0.51 cP at 30° C.).

EXAMPLE 2

Static Settling Experiment

In the glove box, a spent ionic liquid (IL) sample (taken from the catalyst & solids-comprising effluent from an ionic liquid alkylation process as described in WO2011/015639, with the differences that runtime was 178 h, temperature was 24° C., isobutane/butene ratio was 14 and 0.9 kg of HCl was added throughout the run) was homogenized by thorough shaking for 30 sec. Subsequently, three portions of about 20 mL of IL were poured into three 100 mL graduated cylinders. Then three portions of about 20 mL of solvent were added into the graduated cylinders respectively. The solvents were octane, toluene and DCM. The three graduated cylinders were sealed and homogenized by thorough shaking for 30-60 sec at the same time. Then the three graduated cylinders were put aside and phenomena were observed. The settlement of solids was recorded at regular intervals.

2.1 Results and Conclusion

At t=0, the liquid phases in the graduated cylinders were all very well mixed.

At t=10 minutes, the IL+octane mixture had separated in two phases (octane, a bit turbid, at the top, IL with homogeneously dispersed solids at the bottom) of almost equal volume. Thus, the miscibility of octane in IL is very small. Further, the IL+toluene mixture had separated into two phases, of which the toluene phase (top) was about ⅛ of the total volume, and IL with homogeneously dispersed solids (bottom). This means that the miscibility of toluene in IL is relatively large. The IL+DCM mixture was still one phase with homogeneously dispersed solids. Thus, DCM and composite IL are fully miscible.

Hereafter the liquid/liquid levels in the cylinders with octane and toluene added remained constant and the cylinder with DCM added remained one liquid phase. Subsequently, the liquid phases with homogeneously dispersed solids started to separate in a clear liquid mixture of IL and solvent and a turbid liquid phase containing dispersed solids. During settling the interface level between the clear IL/solvent mixture and the turbid phase decreased and the levels are recorded in Table 2.1.

At t=98.5 hours, there was no significant change in the cylinder with the IL+octane mixture. Minor solids settling was observed. In the cylinder with the IL+toluene mixture, settling had continued. Three phases were visible. The toluene phase (top) was still about ⅛ of the total volume. The level of the turbid liquids/solids phase (bottom) was clearly visible at about 25% of the total volume. In the cylinder with the IL+DCM mixture, two phases were visible and the level of the liquid/solids phase had decreased to about 15% of the total volume.

The results of this experiment indicated that the settling time of solids in IL can be significantly reduced by adding DCM or toluene. The changes of the interface between the clear IL/solvent mixture and turbid phase level are recorded in Table 2.1.

TABLE 2.1

The settlement of solids in IL with solvent

| Settling time | IL + n-octane (comparative) | IL + toluene | IL + DCM |
|---|---|---|---|
| | clear IL/solvent mixture and turbid phase interface level, mL | | |
| 10 min | 20.0 | 34.0 | 38.0 |
| 20 min | 20.0 | 34.0 | 35.5 |
| 30 min | 20.0 | 34.0 | 33.2 |
| 40 min | 20.0 | 33.0 | 31.5 |
| 50 min | 20.0 | 32.5 | 29.0 |
| 60 min | 20.0 | 32.0 | 27.0 |
| 1.5 h | 20.0 | 30.0 | 21.5 |
| 2.0 h | 20.0 | 27.5 | 17.5 |
| 2.5 h | 20.0 | 25.0 | 16.0 |
| 3.0 h | 20.0 | 23.0 | 15.6 |
| 3.5 h | 20.0 | 20.5 | 15.0 |
| 4.0 h | 20.0 | 18.5 | 14.5 |
| 4.5 h | 20.0 | 17.0 | 14.0 |
| 5.0 h | 20.0 | 17.0 | 14.0 |
| 5.5 h | 20.0 | 16.0 | 13.5 |
| 6.0 h | 20.0 | 16.0 | 13.5 |
| 7.0 h | 20.0 | 15.5 | 13.0 |

TABLE 2.1-continued

The settlement of solids in IL with solvent

| Settling time | IL + n-octane (comparative) | IL + toluene | IL + DCM |
|---|---|---|---|
| | clear IL/solvent mixture and turbid phase interface level, mL | | |
| 8.0 h | 20.0 | 15.0 | 12.5 |
| 9.0 h | 20.0 | 14.5 | 12.2 |
| 10.0 h | 20.0 | 14.2 | 12.0 |
| 11.0 h | 20.0 | 14.0 | 12.0 |
| 12.0 h | 20.0 | 14.0 | 11.7 |
| 14.0 h | 20.0 | 14.0 | 11.5 |
| 15.0 h | 20.0 | 13.5 | 11.2 |
| 16.5 h | 20.0 | 13.0 | 11.0 |
| 26.5 h | 20.0 | 12.0 | 10.0 |
| 31.0 h | 20.0 | 11.3 | 9.3 |
| 35.0 h | 20.0 | 11.0 | 9.0 |
| 49.5 h | 19.8 | 10.0 | 8.0 |
| 57.5 h | 19.8 | 10.0 | 8.0 |
| 73.5 h | 19.8 | 9.5 | 7.0 |
| 98.5 h | 19.8 | 8.9 | 6.2 |

EXAMPLE 3

Centrifugation Experiment 3.1 Centrifugation without Solvent

In the glove box, a spent ionic liquid (IL) sample similar as started with in Example 2 was homogenized by thoroughly shaking for 30 sec. Subsequently, an amount of about 10 mL of IL was poured into a 10 mL centrifuge tube. The tube was tightly closed, and transferred out of the glove box. Subsequently, the tube was centrifuged at 2000 rpm for 30 min. The settlement of solids was recorded. There was no clear separation visible between solids and ionic liquid. After a further 450 minutes of centrifugation at 2000 rpm, separation of solids was visible. The level of the solids enriched phase was visible at about ⅛ of the total volume.

3.2 Centrifugation with DCM

In the glove box, a spent ionic liquid (IL) sample similar as started with in Example 3.1 was homogenized by thoroughly shaking for 30 sec. Subsequently, an amount of about 6.5 mL of IL was poured into a 10 mL centrifuge tube. Then an amount of about 3.5 mL of DCM was added to the tube. The tube was tightly closed, transferred out of the glove box and thoroughly shaken until a homogeneous mixture was obtained. Subsequently, the tube was centrifuged at 2000 rpm for 15 min. Solid and ionic liquid had clearly separated. The level of the solids was visible at about ⅙ of the total volume.

3.3 Centrifugation with Toluene

In the glove box, a spent ionic liquid (IL) sample similar as started with in Example 3.1 was homogenized by thoroughly shaking for 30 sec. Subsequently, an amount of about 6.5 mL of IL was poured into a 10 mL centrifuge tube. Then an amount of about 3.5 mL of toluene was added to the tube. The tube was tightly closed, transferred out of the glove box and thoroughly shaken until a homogeneous mixture was obtained. Subsequently, the tube was centrifuged at 2000 rpm for 20 min. Solid and ionic liquid had clearly separated. The level of the solids was visible at about ⅙ of the total volume.

The results of experiments 1-3 demonstrate that the centrifugation time of a mixture of solids+IL for separation of the solids can be significantly reduced by adding solvents like DCM or toluene.

EXAMPLES 4-9

Solvent Removal

In the glovebox, 10 mL of DCM were dissolved into 10 mL of fresh composite IL. Then the DCM was extracted from the IL+DCM mixture in two times by using a certain amount of n-octane. The results are show in table 3.

TABLE 3

| Example No. | | Example 4 | Example 5 |
|---|---|---|---|
| Volume of IL, mL | | 10.0 | 10.0 |
| Volume of DCM, mL | | 10.0 | 10.0 |
| Volume of IL + DCM, mL | | 19.9 | 19.9 |
| First extraction | Volume of octane, mL | 10.0 | 20.0 |
| | Volume of IL + DCM after extraction, mL | 14.0 | 13.0 |
| Second extraction | Volume of octane, mL | 10.0 | 20.0 |
| | Volume of IL + DCM after extraction, mL | 11.0 | 10.5 |

In the glovebox, 8 mL of toluene were dissolved into 10 mL of fresh composite IL. Then toluene was extracted from the IL+Toluene mixture in two times by using a certain amount of n-octane.

The results are show in table 4.

TABLE 4

| Example No. | | Example 6 | Example 7 |
|---|---|---|---|
| Volume of IL, mL | | 10.0 | 10.0 |
| Volume of toluene, mL | | 8.0 | 8.0 |
| Volume of IL + toluene, mL | | 18.0 | 18.0 |
| First extraction | Volume of octane, mL | 9.0 | 18.0 |
| | Volume of IL + toluene after extraction, mL | 12 | 11.7 |
| Second extraction | Volume of octane, mL | 9.0 | 18.0 |
| | Volume of IL + toluene after extraction, mL | 10.5 | 10.0 |

In an autoclave (500 mL), 160 mL of toluene was dissolved into 200 mL of fresh composite IL. The stirrer was started (500 rpm), and then the autoclave was controlled to the setting of 30° C. Isobutane was continuously pumped into the autoclave by the plunger pump (500 mL/h). The pressure in the autoclave was maintained at 0.5 MPa. In the top part of the autoclave phase separation between the ionic liquid and the hydrocarbon phase took place. Toluene was extracted from the IL+Toluene mixture by using a certain amount of isobutane. After extraction, isobutane was removed by evaporation in the autoclave, then the volume of IL+Toluene was measured. (See FIG. 5) The results are show in table 5.

TABLE 5

| Example No. | Example 8 | Example 9 |
|---|---|---|
| Volume of IL, mL | 200 | 200 |
| Volume of toluene, mL | 160 | 160 |
| Volume of isobutane, mL | 1000 | 2000 |
| Volume of IL + toluene after extraction, mL | 211 | 198 |

The results of experiments 4-9 show that the solvent added to lower the viscosity as used in experiments 1-3 can be removed successfully from the ionic liquid by extraction.

EXAMPLE 5

5.1 The Separation of Solids and Liquid for Spent Ionic Liquid

In the glove box a spent (used) ionic liquid (IL) sample (taken from the catalyst & solids-comprising effluent from an ionic liquid alkylation process as described in WO2011/015639, with the differences that runtime was 42 h, the temperature was 24° C., isobutene/butane ratio was 16 and 0.7 kg of HCl was added throughout the run) was homogenized by thorough shaking for 10-15 sec. Subsequently, an amount of about 8 mL of IL was poured into a 10 mL centrifuge tube. The tube was tightly closed, transferred out of the glovebox and centrifuged at 4000 rpm for 45 min.

A sample of 141.1 mg of IL was taken from the top 5 mm of the liquid in the tube and transferred into a weighed 25 mL round bottom flask. The remaining liquid in the centrifuge tube was decanted from the solid into a weighed 10 mL bottle and the tube was drained by clamping it upside down for 30 min. The centrifuge tube was weighed to determine the amount of "Isolated Paste" (1.379 g).

5.2 Isolation of Solids and IL from Paste

In the glovebox 10 g of DCM was added to the isolated paste of example 5.1 in the centrifuge tube. The tube was tightly closed, transferred out of the glovebox and thoroughly shaken until a fully dispersed solid material was obtained. Subsequently the tube was centrifuged at 2000 rpm for 10 min, and then transferred back into the glovebox. The DCM extract was decanted in a round bottom flask (100 mL). The residue was once more extracted with about 10 g of DCM as described above. The DCM extracts were combined, transferred to a Schlenk line and evaporated under vacuum at 40° C. The residue was transferred back into the glovebox and weighed (0.921 g) ("Isolated IL from paste").

The extraction residue in the centrifuge tube was also dried (at room temperature) under vacuum and weighed (0.450 g) ("Isolated solids from paste").

5.3 The Destruction of IL to Prepare Solutions for Elemental Analysis

The round bottom flask containing the IL fraction of example 5.1 was closed by a septum inlet adapter. The flask was cooled to about 0-5° C. in about 15 min. Then, 5 mL of cooled demi-water was measured in a syringe and transferred to the sample flask via the septum. After injection of the water, the flask was moderately swirled until a homogenized solution was obtained. The inlet adapter was removed and the solution in the flask was diluted to about 10-15 mL with demi-water. Subsequently the solution was acidified to pH 2-1, using 3 drops of nitric acid (65%). A stir-bar was added and air was gently bubbled through the stirred solution for 30 min. The solution was quantitatively transferred into a bottle (100 mL) using demi-water rinsing.

The total amount of water was dosed to arrive at 100.0 g sample solution. The bottle was closed and homogenized.

This solution was suitable for chloride analysis via coulometric titration.

Next, an amount of 10.00 g of the obtained solution was diluted with demi-water to 100.0 g in a bottle (100 mL). The 1:10 diluted solution was suitable for Al and Cu analysis by ICP-AES. The results are listed in Table 6.

5.4 Preparation of Solution from "Isolated Solids from Paste" for Elemental Analysis Example 5.3 was repeated for preparation of a solution from 111.9 mg of the isolated solids of example 5.2 for elemental analysis.

The results are listed in Table 6.

5.5 Preparation of Solution from "Isolated IL from Paste" for Elemental Analysis Example 5.3 was repeated for preparation of a solution from 156.9 mg of the isolated IL of example 5.2 for elemental analysis.

The results are listed in Table 6.

TABLE 6

Result of elemental analysis

| Sample | Cl, wt % | Al, wt % | Cu, wt % | Sum, wt % | Mass, g |
|---|---|---|---|---|---|
| Isolated IL | 51.8 | 11.6 | 1.6 | 65.0 | 10.40 |
| Isolated IL from paste | 52.4 | 11.5 | 1.4 | 65.2 | 0.92 |
| Isolated solids from paste | 37.8 | 0.6 | 51.4 | 89.8 | 0.45 |

The results of examples 5.1-5.5 demonstrate that between "Isolated IL" and "Isolated IL from Paste", there is no significant difference in the results from elemental analysis. This indicates that IL can be extracted from the paste with DCM and easily recovered by evaporation of DCM.

EXAMPLE 6

6.1 The Alkylation Test to Obtain Used IL

About 400 g of fresh composite IL was placed into an autoclave (1000 mL). The stirrer was started (900 rpm), and then the autoclave was controlled to the setting of 25° C. Isobutane/butene feed (Isobutane/2-butene ratio was 9.3) was continuously pumped into the autoclave by a plunger pump at a rate of 700 mL/h. The pressure in the autoclave was maintained at 0.6 MPa.

When the autoclave was introduced with 2.0 kg of isobutane/butene feed (isobutane/2-butene ratio was 9.3) a sample of the upper part of the autoclave (containing the hydrocarbon phase) was taken and this sample (sample 1) was analyzed by gas chromatography. The results are shown in Table 7.

When the autoclave was introduced with 15 kg of isobutane/butene feed (Isobutane/2-butene ratio was 9.3) the pump and the stirrer were stopped. Phase separation took place, where after the lower phase, containing spent IL, was isolated.

6.2 The Isolation of IL from Paste

The spent IL of example 6.1 was centrifuged at 4000 rpm for 5 hours. The 301.12 g "isolated IL" was decanted from the paste into a bottle and 85.28 g of paste was obtained.

In the glovebox about 50 g of DCM was added to the paste in the centrifuge bottle. The bottle was tightly closed, transferred out of the glove box and thoroughly shaken until a solid material was fully dispersed. Subsequently the bottle was centrifuged at 4000 rpm for 30 minutes, and then transferred into the glovebox. The DCM extracts was decanted in a round bottom flask (500 mL). The residue was eight times more extracted with about 50 g of DCM as described above. The DCM extracts were combined, and evaporated under vacuum at room temperature. The residue was weighed (62.24 g) ("Isolated IL from paste").

6.3 The Alkylation Test of "Isolated IL from Paste"

"Isolated IL from paste" sample of example 6.2 was placed into an autoclave (280 mL). The stirrer was started (1000 rpm) and then the autoclave was controlled at 25° C. Isobutane/butene feed (Isobutane/2-butene ratio was 9.3) was continuously pumped into the autoclave by a plunger pump at a rate of 500 mL/h. Example 6.1 was repeated for the alkylation test of "isolated IL from paste".

When the autoclave was introduced with 0.5 kg of isobutane feed/butene feed (isobutane/2-butene ratio was 9.3) a sample was taken and this sample (sample 2) was analyzed by gas chromatography. The results are shown in Table 7.

6.4 The Alkylation Test of Isolated IL

About 60 g of isolated IL of example 6.2 was placed into an autoclave (280 mL). The stirrer was started (1000 rpm) and then the autoclave was controlled at 25° C. Isobutane/butene feed (isobutane/2-butene ratio was 9.3) was continuously pumped into the autoclave by a plunger pump at a rate of 500 mL/h. Example 6.1 was repeated for the alkylation test of "isolated IL".

When the autoclave was introduced with 0.5 kg of isobutane feed/butene feed (isobutane/2-butene ratio was 9.3) a sample was taken and this sample (sample 3) was analyzed by gas chromatography. The results are shown in Table 7.

6.5 The Alkylation Test of Fresh IL

About 60 g of fresh composite IL was placed into an autoclave (280 mL). The alkylation conditions and procedures are same as examples 6.3 and 6.4. A sample (sample 4) was taken after 0.5 kg of isobutane/butene feed (isobutane/2-butene ratio was 9.3) was introduced to the autoclave. This sample 4 was analyzed by gas chromatography and the results are shown in Table 7.

TABLE 7

Composition of alkylate

| Sample | C5-C7 wt % | TMP wt % | DMH wt % | T/D | C9+ wt % | RON |
|---|---|---|---|---|---|---|
| 1 | 10.9 | 73.0 | 10.8 | 6.8 | 5.3 | 94.4 |
| 2 | 12.1 | 70.7 | 11.6 | 6.1 | 5.6 | 93.1 |

TABLE 7-continued

| | Composition of alkylate | | | | | |
|---|---|---|---|---|---|---|
| Sample | C5-C7 wt % | TMP wt % | DMH wt % | T/D | C9+ wt % | RON |
| 3 | 11.8 | 71.2 | 11.6 | 6.1 | 5.4 | 93.4 |
| 4 | 9.8 | 75.1 | 10.9 | 6.9 | 4.2 | 95.0 |

The selectivities of IL, extracted from solid (paste) and isolated by centrifuging of used IL, are very similar. The examples 6.1-6.5 shows that IL extracted from the paste can be reused in the ILA process without significant loss of selectivity.

That which is claimed is:

1. A process for preparing alkylate comprising the subsequent steps (a), (b) and (c):
    (a) an alkylation step, wherein in a reaction zone a hydrocarbon mixture comprising at least an isoparaffin and an olefin is reacted with an ionic liquid catalyst to obtain an effluent comprising alkylate and solids, which latter are formed as side products in the alkylation step;
    (b) a separation step, wherein at least part of the alkylate-comprising effluent coming from the reaction zone is separated in a separator unit into a hydrocarbon-rich phase and an ionic liquid catalyst-rich phase which latter phase also comprises solids formed as side products during the alkylation reaction; and
    (c) a solids removal step, wherein the solids in ionic liquid catalyst-rich phase are separated from the ionic liquid catalyst using a suitable separating device;
    wherein the process further comprises a step following the separation step (b) and prior to the solids removal step (c), wherein an amount of an organic solvent is added to the ionic liquid catalyst-rich phase, which organic solvent has a viscosity which is significantly lower than that of the ionic liquid and which solvent is at least partially miscible with the ionic liquid.

2. The process of claim 1, wherein the organic solvent is selected from aromatic solvents, halogenated aliphatic hydrocarbons, acetonitrile or mixtures thereof.

3. The process of claim 1, wherein the mass fraction of the organic solvent, when added to the ionic liquid catalyst-rich phase, is 5-60 wt %.

4. The process of claim 1, wherein the organic solvent is added via a pipeline by in-line mixing in the pipeline connection between the separator unit and the solid separating device.

5. The process of claim 1, wherein the solid separating device is a centrifugation device.

6. The process of claim 1, further comprising removal of the organic solvent after solids removal.

7. The process of claim 6, wherein the organic solvent is removed by a distillation unit or isobutane extraction followed by distillation.

8. The process of claim 7, wherein the organic solvent is purified by distillation device, from which the heavy ends (high boiling point components) is removed.

9. The process of claim 6, wherein the organic solvent is recycled to separator unit.

10. The process of claim 6, wherein the resulting ionic liquid is recycled to the reaction zone and re-used in the alkylation process.

* * * * *